(12) United States Patent
Hicks

(10) Patent No.: US 8,998,866 B2
(45) Date of Patent: Apr. 7, 2015

(54) PROVISION OF WOUND FILLER

(75) Inventor: John Kenneth Hicks, Heslington (GB)

(73) Assignee: Smith & Nephew PLC, London (GB)

( * ) Notice: Subject to any disclaimer, the term of this patent is extended or adjusted under 35 U.S.C. 154(b) by 0 days.

(21) Appl. No.: 13/806,722

(22) PCT Filed: Jul. 1, 2011

(86) PCT No.: PCT/GB2011/000998
§ 371 (c)(1),
(2), (4) Date: Dec. 21, 2012

(87) PCT Pub. No.: WO2012/001371
PCT Pub. Date: Jan. 5, 2012

(65) Prior Publication Data
US 2013/0116641 A1    May 9, 2013

(30) Foreign Application Priority Data

Jul. 2, 2010 (GB) .................................. 1011173.0

(51) Int. Cl.
*A61M 1/00* (2006.01)
*A61F 13/00* (2006.01)
*A61L 26/00* (2006.01)
(52) U.S. Cl.
CPC ....... *A61F 13/00068* (2013.01); *A61L 26/0085* (2013.01)
(58) Field of Classification Search
USPC .......... 604/313, 317, 319, 543, 304; 128/898, 128/897
See application file for complete search history.

(56) References Cited

U.S. PATENT DOCUMENTS

| | | |
|---|---|---|
| 3,274,155 A | 9/1966 | Saunders et al. |
| 3,646,155 A | 2/1972 | Scott et al. |
| 3,783,870 A | 1/1974 | Schachet |
| 3,808,178 A | 4/1974 | Gaylord |
| 3,809,086 A | 5/1974 | Schachet et al. |
| 3,809,087 A | 5/1974 | Lewis, Jr. |
| 3,928,629 A | 12/1975 | Chandra et al. |
| 4,073,294 A | 2/1978 | Stanley et al. |
| 4,117,551 A | 9/1978 | Books et al. |
| 4,266,545 A | 5/1981 | Moss |
| 4,278,089 A | 7/1981 | Huck et al. |
| 4,392,860 A | 7/1983 | Huck et al. |
| 4,529,553 A | 7/1985 | Faltynek |
| 4,538,920 A | 9/1985 | Drake et al. |
| 4,569,674 A | 2/1986 | Phillips et al. |
| 4,578,060 A | 3/1986 | Huck et al. |
| 4,655,754 A | 4/1987 | Richmond et al. |

(Continued)

FOREIGN PATENT DOCUMENTS

| | | |
|---|---|---|
| DE | 3 838 587 A1 | 5/1990 |
| EP | 0 251 810 A2 | 1/1988 |

(Continued)

OTHER PUBLICATIONS

U.S. Appl. No. 13/627,473, filed Sep. 26, 2012, Blott et al.

(Continued)

*Primary Examiner* — Leslie Deak
*Assistant Examiner* — Kai Weng
(74) *Attorney, Agent, or Firm* — Knobbe Martens Olson & Bear LLP

(57) ABSTRACT

A process of manufacturing a wound dressing filler and/or wound dressing.

18 Claims, 3 Drawing Sheets

(56) References Cited

U.S. PATENT DOCUMENTS

| | | |
|---|---|---|
| 4,661,093 A | 4/1987 | Beck et al. |
| 4,713,052 A | 12/1987 | Beck et al. |
| 4,714,739 A | 12/1987 | Arkles |
| 4,753,536 A | 6/1988 | Spehar et al. |
| 4,767,026 A | 8/1988 | Keller |
| 4,771,919 A | 9/1988 | Ernst |
| 4,798,583 A | 1/1989 | Beck et al. |
| 4,826,494 A | 5/1989 | Richmond et al. |
| 4,872,450 A | 10/1989 | Austad |
| 4,923,444 A | 5/1990 | Daoud et al. |
| 4,936,834 A | 6/1990 | Beck et al. |
| 4,969,880 A | 11/1990 | Zamierowski |
| 5,033,650 A | 7/1991 | Colin et al. |
| 5,064,653 A | 11/1991 | Sessions et al. |
| 5,080,493 A | 1/1992 | McKown et al. |
| 5,089,606 A | 2/1992 | Cole et al. |
| 5,100,395 A | 3/1992 | Rosenberg |
| 5,141,503 A | 8/1992 | Sewell, Jr. |
| 5,145,933 A | 9/1992 | Grisoni et al. |
| 5,153,231 A | 10/1992 | Bouquet et al. |
| 5,249,709 A | 10/1993 | Duckworth et al. |
| 5,333,760 A | 8/1994 | Simmen et al. |
| 5,348,392 A | 9/1994 | Bouquet et al. |
| 5,397,848 A | 3/1995 | Yang et al. |
| 5,549,584 A | 8/1996 | Gross |
| 5,582,596 A | 12/1996 | Fukunaga et al. |
| 5,609,271 A | 3/1997 | Keller et al. |
| 5,636,643 A | 6/1997 | Argenta et al. |
| 5,645,081 A | 7/1997 | Argenta et al. |
| 5,840,777 A | 11/1998 | Eagles et al. |
| D406,899 S | 3/1999 | Cottle |
| RE36,235 E | 6/1999 | Keller et al. |
| 5,944,703 A | 8/1999 | Dixon et al. |
| 6,024,731 A | 2/2000 | Seddon et al. |
| 6,135,116 A | 10/2000 | Vogel et al. |
| D434,150 S | 11/2000 | Tumey et al. |
| 6,142,982 A | 11/2000 | Hunt et al. |
| D439,341 S | 3/2001 | Tumey et al. |
| 6,252,129 B1 | 6/2001 | Coffee |
| 6,261,276 B1 | 7/2001 | Reitsma |
| 6,345,623 B1 | 2/2002 | Heaton et al. |
| 6,391,294 B1 | 5/2002 | Dettmar et al. |
| 6,398,761 B1 | 6/2002 | Bills et al. |
| 6,458,109 B1 | 10/2002 | Henley et al. |
| 6,486,285 B2 | 11/2002 | Fujita |
| 6,527,203 B2 | 3/2003 | Hurray et al. |
| 6,553,998 B2 | 4/2003 | Heaton et al. |
| 6,564,972 B2 | 5/2003 | Sawhney et al. |
| 6,569,113 B2 | 5/2003 | Wirt et al. |
| 6,629,774 B1 | 10/2003 | Guruendeman |
| 6,648,862 B2 | 11/2003 | Watson |
| 6,685,681 B2 | 2/2004 | Lockwood et al. |
| 6,695,823 B1 | 2/2004 | Lina et al. |
| 6,698,622 B2 | 3/2004 | Sawhney et al. |
| 6,730,299 B1 | 5/2004 | Tayot et al. |
| 6,732,887 B2 | 5/2004 | Bills |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,820,766 B2 | 11/2004 | Keller et al. |
| 6,824,533 B2 | 11/2004 | Risk, Jr. et al. |
| 6,840,462 B2 | 1/2005 | Hurray et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,117,869 B2 | 10/2006 | Heaton et al. |
| 7,132,170 B2 | 11/2006 | Parker |
| 7,175,336 B2 | 2/2007 | Voellmicke et al. |
| 7,316,330 B2 | 1/2008 | Muller et al. |
| 7,387,432 B2 | 6/2008 | Lu et al. |
| 7,396,507 B2 | 7/2008 | Grunwald et al. |
| 7,524,315 B2 | 4/2009 | Blott et al. |
| 7,543,843 B2 | 6/2009 | Keshavaraj et al. |
| 7,635,343 B2 | 12/2009 | McIntosh et al. |
| 7,674,837 B2 | 3/2010 | Gaserod et al. |
| 7,700,819 B2 | 4/2010 | Ambrosio et al. |
| 7,708,724 B2 | 5/2010 | Weston |
| 7,708,940 B2 | 5/2010 | Grunwald et al. |
| 7,717,313 B2 | 5/2010 | Criscuolo et al. |
| 7,722,582 B2 | 5/2010 | Lina et al. |
| 7,758,554 B2 | 7/2010 | Lina et al. |
| 7,776,028 B2 | 8/2010 | Miller et al. |
| 7,882,983 B2 | 2/2011 | Reidt et al. |
| 7,922,743 B2 | 4/2011 | Heinrich et al. |
| 7,954,672 B2 | 6/2011 | Keller |
| 8,007,164 B2 | 8/2011 | Miyano et al. |
| 8,025,650 B2 | 9/2011 | Anderson et al. |
| 8,074,843 B2 | 12/2011 | Keller |
| 8,096,979 B2 | 1/2012 | Lina et al. |
| 8,100,887 B2 | 1/2012 | Weston et al. |
| 8,162,909 B2 * | 4/2012 | Blott et al. .................. 604/319 |
| 8,225,981 B2 | 7/2012 | Criscuolo et al. |
| 8,282,611 B2 | 10/2012 | Weston |
| 8,286,832 B2 | 10/2012 | Keller |
| 8,303,552 B2 | 11/2012 | Weston |
| 8,481,801 B2 | 7/2013 | Addison et al. |
| 8,540,699 B2 | 9/2013 | Miller et al. |
| 8,613,734 B2 | 12/2013 | Lina et al. |
| 8,708,998 B2 | 4/2014 | Weston et al. |
| 8,801,685 B2 | 8/2014 | Armstrong et al. |
| 2001/0004082 A1 | 6/2001 | Keller et al. |
| 2002/0010299 A1 | 1/2002 | Guyuron et al. |
| 2002/0038826 A1 | 4/2002 | Hurray et al. |
| 2002/0143286 A1 | 10/2002 | Tumey |
| 2002/0145007 A1 | 10/2002 | Sawhney et al. |
| 2002/0146662 A1 * | 10/2002 | Radl et al. .................. 433/90 |
| 2002/0183702 A1 | 12/2002 | Henley et al. |
| 2002/0198490 A1 | 12/2002 | Wirt et al. |
| 2003/0093041 A1 | 5/2003 | Risk, Jr. et al. |
| 2003/0183653 A1 | 10/2003 | Bills |
| 2003/0212357 A1 | 11/2003 | Pace |
| 2004/0006319 A1 | 1/2004 | Lina et al. |
| 2004/0033466 A1 | 2/2004 | Shellard et al. |
| 2004/0073151 A1 | 4/2004 | Weston |
| 2004/0121438 A1 | 6/2004 | Quirk |
| 2004/0167617 A1 | 8/2004 | Voellmicke et al. |
| 2004/0171998 A1 | 9/2004 | Marasco, Jr. |
| 2004/0243073 A1 | 12/2004 | Lockwood et al. |
| 2005/0010153 A1 | 1/2005 | Lockwood et al. |
| 2005/0020955 A1 | 1/2005 | Sanders et al. |
| 2005/0070858 A1 | 3/2005 | Lockwood et al. |
| 2005/0085795 A1 | 4/2005 | Lockwood et al. |
| 2005/0100692 A1 | 5/2005 | Parker |
| 2005/0148913 A1 | 7/2005 | Weston |
| 2005/0163904 A1 | 7/2005 | Walker et al. |
| 2005/0203452 A1 | 9/2005 | Weston et al. |
| 2005/0222527 A1 | 10/2005 | Miller et al. |
| 2005/0222528 A1 | 10/2005 | Weston |
| 2005/0230422 A1 | 10/2005 | Muller et al. |
| 2005/0261642 A1 | 11/2005 | Weston |
| 2006/0015087 A1 | 1/2006 | Risk, Jr. et al. |
| 2006/0100586 A1 | 5/2006 | Karpowicz et al. |
| 2006/0173253 A1 | 8/2006 | Ganapathy et al. |
| 2006/0217016 A1 | 9/2006 | Lin et al. |
| 2006/0253082 A1 | 11/2006 | Mcintosh et al. |
| 2006/0273109 A1 | 12/2006 | Keller |
| 2007/0164047 A1 | 7/2007 | Reidt et al. |
| 2007/0186404 A1 * | 8/2007 | Drew et al. .................. 29/557 |
| 2007/0219513 A1 | 9/2007 | Lina et al. |
| 2007/0225663 A1 | 9/2007 | Watt et al. |
| 2007/0237811 A1 | 10/2007 | Scherr |
| 2008/0004549 A1 | 1/2008 | Anderson et al. |
| 2008/0089173 A1 | 4/2008 | Lu et al. |
| 2008/0232187 A1 | 9/2008 | Miyano et al. |
| 2008/0279807 A1 | 11/2008 | Belcheva et al. |
| 2008/0287880 A1 | 11/2008 | Keller |

(56) References Cited

U.S. PATENT DOCUMENTS

| | | |
|---|---|---|
| 2008/0314929 A1 | 12/2008 | Keller |
| 2009/0020561 A1 | 1/2009 | Keller |
| 2009/0093550 A1 | 4/2009 | Rolfes et al. |
| 2009/0134186 A1 | 5/2009 | Keller |
| 2009/0157017 A1 | 6/2009 | Ambrosio |
| 2009/0275872 A1 | 11/2009 | Addison et al. |
| 2009/0287181 A1* | 11/2009 | Kagan ............................ 604/506 |
| 2010/0022972 A1 | 1/2010 | Lina et al. |
| 2010/0036334 A1* | 2/2010 | Heagle et al. .................. 604/319 |
| 2010/0125259 A1* | 5/2010 | Olson ............................ 604/319 |
| 2010/0135915 A1 | 6/2010 | Greener |
| 2010/0137775 A1 | 6/2010 | Hu et al. |
| 2010/0230467 A1 | 9/2010 | Criscuolo et al. |
| 2010/0268177 A1* | 10/2010 | Hall et al. ...................... 604/313 |
| 2011/0028919 A1 | 2/2011 | Johnnison et al. |
| 2011/0036889 A1 | 2/2011 | Heinrich et al. |
| 2011/0118683 A1 | 5/2011 | Weston |
| 2011/0147432 A1 | 6/2011 | Heinrich et al. |
| 2011/0147435 A1 | 6/2011 | Heinrich et al. |
| 2011/0251567 A1 | 10/2011 | Blott et al. |
| 2012/0083755 A1 | 4/2012 | Lina et al. |
| 2012/0123356 A1 | 5/2012 | Greener |
| 2013/0023841 A1 | 1/2013 | Johnson et al. |
| 2013/0096519 A1 | 4/2013 | Blott et al. |
| 2013/0274688 A1 | 10/2013 | Weston |
| 2013/0310780 A1 | 11/2013 | Phillips |
| 2013/0310781 A1 | 11/2013 | Phillips |
| 2014/0012214 A1 | 1/2014 | Miller et al. |
| 2014/0228792 A1 | 8/2014 | Weston et al. |

FOREIGN PATENT DOCUMENTS

| | | |
|---|---|---|
| EP | 0 355 536 B1 | 2/1990 |
| EP | 0 425 164 A1 | 5/1991 |
| EP | 0 521 434 A1 | 7/1993 |
| EP | 0 425 164 B1 | 9/1994 |
| EP | 0 648 122 B1 | 4/1995 |
| EP | 0 690 736 B1 | 1/1996 |
| EP | 0 724 888 B1 | 8/1996 |
| EP | 0 754 064 B1 | 1/1997 |
| EP | 0 772 464 B1 | 5/1997 |
| EP | 0 537 559 B1 | 1/1998 |
| EP | 0 856 318 B1 | 8/1998 |
| EP | 0 858 810 B1 | 8/1998 |
| EP | 0 876 165 B1 | 11/1998 |
| EP | 0 888 141 B1 | 1/1999 |
| EP | 0 912 251 B1 | 5/1999 |
| EP | 1 007 015 B1 | 6/2000 |
| EP | 1 021 180 B1 | 7/2000 |
| EP | 1 029 585 B1 | 8/2000 |
| EP | 1 030 657 B1 | 8/2000 |
| EP | 1 085 925 B1 | 3/2001 |
| EP | 1 105 110 B1 | 6/2001 |
| EP | 1 105 171 B1 | 6/2001 |
| EP | 1 105 180 B1 | 6/2001 |
| EP | 1 107 813 B1 | 6/2001 |
| EP | 1 138 336 B1 | 10/2001 |
| EP | 1 156 839 B1 | 11/2001 |
| EP | 0 564 502 B1 | 1/2002 |
| EP | 1 218 437 B1 | 7/2002 |
| EP | 1 306 123 A1 | 2/2003 |
| EP | 1 440 737 A1 | 7/2004 |
| EP | 1 632 252 B1 | 3/2006 |
| EP | 1 633 830 A2 | 3/2006 |
| EP | 1 758 637 B1 | 3/2007 |
| EP | 1 798 835 A1 | 6/2007 |
| EP | 1 978 046 A2 | 10/2008 |
| EP | 1 988 125 A2 | 11/2008 |
| EP | 1 993 512 A2 | 11/2008 |
| EP | 2 111 804 A2 | 10/2009 |
| EP | 2 255 837 A1 | 12/2010 |
| EP | 1 374 914 B1 | 3/2011 |
| EP | 2 335 747 A1 | 6/2011 |
| EP | 1 169 071 | 2/2012 |
| EP | 2 643 412 A1 | 10/2013 |
| GB | 2288734 A | 11/1995 |
| GB | 2307180 A | 5/1997 |
| GB | 2329127 A | 3/1999 |
| GB | 2422545 B | 8/2006 |
| GB | 2424581 B | 10/2006 |
| GB | 2424582 B | 10/2006 |
| GB | 2435419 B | 2/2007 |
| JP | 2005 261376 A | 9/2005 |
| WO | WO 92/09651 | 6/1992 |
| WO | WO 93/06802 | 4/1993 |
| WO | WO 93/09176 | 5/1993 |
| WO | WO 94/20133 | 9/1994 |
| WO | WO 95/03838 | 2/1995 |
| WO | WO 96/00760 | 1/1996 |
| WO | WO 96/40174 | 12/1996 |
| WO | WO 97/03717 | 2/1997 |
| WO | WO 97/13520 | 4/1997 |
| WO | WO 97/33922 | 9/1997 |
| WO | WO 97/42986 | 11/1997 |
| WO | WO 98/06444 | 2/1998 |
| WO | WO 99/15121 | 4/1999 |
| WO | WO 99/17698 | 4/1999 |
| WO | WO 99/23010 | 5/1999 |
| WO | WO 99/30629 | 6/1999 |
| WO | WO 99/47097 | 9/1999 |
| WO | WO 99/64081 | 12/1999 |
| WO | WO 99/65536 | 12/1999 |
| WO | WO 00/09199 | 2/2000 |
| WO | WO 00/38752 | 7/2000 |
| WO | WO 00/61206 | 10/2000 |
| WO | WO 00/62827 | 10/2000 |
| WO | WO 00/64396 | 11/2000 |
| WO | WO 01/05443 | 1/2001 |
| WO | WO 01/35882 | 5/2001 |
| WO | WO 01/41779 | 6/2001 |
| WO | WO 01/62312 | 8/2001 |
| WO | WO 01/66017 | 9/2001 |
| WO | WO 02/00268 | 1/2002 |
| WO | WO 02/02079 | 1/2002 |
| WO | WO 02/09765 | 2/2002 |
| WO | WO 02/20026 | 3/2002 |
| WO | WO 02/34304 | 5/2002 |
| WO | WO 02/064182 | 8/2002 |
| WO | WO 02/094256 | 11/2002 |
| WO | WO 02/102864 | 12/2002 |
| WO | WO 03/020358 | 3/2003 |
| WO | WO 03/041686 | 5/2003 |
| WO | WO 03/063923 | 8/2003 |
| WO | WO 03/071991 | 9/2003 |
| WO | WO 2004/012678 | 2/2004 |
| WO | WO 2004/032977 | 4/2004 |
| WO | WO 2004/045498 | 6/2004 |
| WO | WO 2004/054632 | 7/2004 |
| WO | WO 2004/091370 | 10/2004 |
| WO | WO 2004/108175 | 12/2004 |
| WO | WO 2005/009225 | 2/2005 |
| WO | WO 2005/017000 | 2/2005 |
| WO | WO 2005/018695 | 3/2005 |
| WO | WO 2005/021042 | 3/2005 |
| WO | WO 2005/034875 | 4/2005 |
| WO | WO 2005/079877 | 9/2005 |
| WO | WO 2005/118011 | 12/2005 |
| WO | WO 2006/002528 | 1/2006 |
| WO | WO 2006/013084 | 2/2006 |
| WO | WO 2006/014534 | 2/2006 |
| WO | WO 2006/030054 | 3/2006 |
| WO | WO 2006/034128 | 3/2006 |
| WO | WO 2006/042169 | 4/2006 |
| WO | WO 2006/079822 | 8/2006 |
| WO | WO 2006/107387 | 10/2006 |
| WO | WO 2006/116524 | 11/2006 |
| WO | WO 2006/131747 | 12/2006 |
| WO | WO 2006/135506 | 12/2006 |
| WO | WO 2007/030601 | 3/2007 |
| WO | WO 2007/031757 | 3/2007 |
| WO | WO 2007/089103 | 8/2007 |
| WO | WO 2007/092405 | 8/2007 |
| WO | WO 2007/103208 | 9/2007 |

(56) References Cited

FOREIGN PATENT DOCUMENTS

| | | |
|---|---|---|
| WO | WO 2007/106594 | 9/2007 |
| WO | WO 2007/123598 | 11/2007 |
| WO | WO 2007/124198 | 11/2007 |
| WO | WO 2007/139812 | 12/2007 |
| WO | WO 2008/032232 | 3/2008 |
| WO | WO 2008/040020 | 4/2008 |
| WO | WO 2008/041926 | 4/2008 |
| WO | WO 2008/057600 | 5/2008 |
| WO | WO 2008/070270 | 6/2008 |
| WO | WO 2008/076407 | 6/2008 |
| WO | WO 2008/082444 | 7/2008 |
| WO | WO 2008/091521 | 7/2008 |
| WO | WO 2008/103891 | 8/2008 |
| WO | WO 2008/133918 | 11/2008 |
| WO | WO 2008/134544 | 11/2008 |
| WO | WO 2008/134774 | 11/2008 |
| WO | WO 2009/007785 | 1/2009 |
| WO | WO 2009/038783 | 3/2009 |
| WO | WO 2009/042514 | 4/2009 |
| WO | WO 2009/047655 | 4/2009 |
| WO | WO 2009/052193 | 4/2009 |
| WO | WO 2009/060327 | 5/2009 |
| WO | WO 2009/073401 | 6/2009 |
| WO | WO 2009/083544 | 7/2009 |
| WO | WO 2009/088726 | 7/2009 |
| WO | WO 2009/098595 | 8/2009 |
| WO | WO 2009/102952 | 8/2009 |
| WO | WO 2009/120432 | 10/2009 |
| WO | WO 2009/123720 | 10/2009 |
| WO | WO 2009/124407 | 10/2009 |
| WO | WO 2009/126102 | 10/2009 |
| WO | WO 2009/156709 | 12/2009 |
| WO | WO 2009/158131 | 12/2009 |
| WO | WO 2011/072840 | 6/2011 |
| WO | WO 2012/001371 | 1/2012 |
| WO | WO 2012/069793 | 5/2012 |
| WO | WO 2012/069794 | 5/2012 |

OTHER PUBLICATIONS

Australian First Office Action for Australian Application No. 2008240389 dated Sep. 10, 2012 (5 pages).
English Translation of State Intellectual Property Office, P.R. China Second Office Action for PCT/GB2008/050268 issued on Apr. 6, 2012 (3 pages).
English Translation of State Intellectual Property Office, P. R. China First Office Action for PCT/GB2008/050268 issued on May 6, 2011 (20 pages).
First European Office Action for European Application No. 08 737 193.6 dated Jun. 7, 2010 (3 pages).
International Search Report for PCT Application No. PCT/GB2011/000998, mailed Nov. 21, 2011.
International Preliminary Report on Patentability for PCT/GB2008/050268 issued Oct. 27, 2009.
International Search Report re PCT/GB2008/050268, mailed Oct. 30, 2008.
Jahns et al., Poster "Problemwundversorgung mit einem neuen anschmiegsamen Silikonschaumverband mit Anwendung der Vakuumtechnik," 2nd Congress of German Wound Treatment Society 1998.
Khan, et al., "Influence of Chitosan Molecular Weight on its Physical Properties", EIMJM (2003); 2(1); pp. 1-8.
Second European Office Action for European Application No. 08 737 193.6, dated Feb. 21, 2012 (6 pages).
Sogias, et al., "Exploring the Factors Affecting the Solubility of Chitosan in Water", Macromol. Chem. Phys. (2010); 211; pp. 426-433.
Wooding-Scott, Margaret, et al., "No Wound is Too Big for Resourceful Nurses," RN Dec. 1988, pp. 22-25 USA.
Meissner, J., X-ray Sterilisation dated Mar. 1, 2008. Retrieved from http://www.emdt.co.uk/article/x-ray-sterilisation.
Dethier et al., X-ray Sterilisation. The Technology of the Future dated Feb. 1, 2010. Retrieved from http://www.emdt.co.uk/article/x-ray-sterilisation-technology-future.
US 6,216,701, 04/2001, Heaton et al. (withdrawn)

* cited by examiner

PROVISION OF WOUND FILLER

CROSS-REFERENCE TO RELATED APPLICATIONS

This application is a U.S. National Phase of the PCT International Application No. PCT/GB2011/000998, filed on Jul. 1, 2011, and which claims priority to application GB 1011173.0, filed on Jul. 2, 2010.

FIELD OF THE INVENTION

The present invention relates to a method and apparatus for providing a wound filler at a wound site prior to the application of negative pressure wound therapy. In particular, but not exclusively, the present invention relates to a method of injecting filler material through a pre-arranged drape at a wound site.

BACKGROUND OF THE INVENTION

Negative pressure wound therapy (NPWT) has become widely used as a treatment mechanism for chronic or acute wounds. The therapy utilises the application of negative pressure to a wound. This causes mechanical contraction of the wound and/or micro-deformation of the wound-bed stimulating increased blood flow in the surrounding tissues and formation of new granulation tissue. Fluid and other deleterious material is removed from the wound. The wound site is also protected from external contaminants. Often the negative pressure is transmitted to and fluid removed from the wound-bed via a porous wound filler.

Known wound fillers are composed of either foam or gauze and both of these options work well in transmitting negative pressure and removing fluid.

Typically foam fillers, which tend to be of an open celled and possibly reticulated nature, are cut to shape and then packed into the wound cavity. Alternatively, if gauze is used then a pad of gauze is formed and then packed into the cavity. The wound and filler is then sealed using a drape and negative pressure applied via tubes connected in some way through the drape to a source of negative pressure such as a vacuum pump. A single or multi-lumen tube can be utilised to connect the wound site to the negative pressure source. Optionally, the tube or tubes can be fixed to the wound site via a coupling, sometimes referred to as a suction head, adhered to the top of the drape. Alternatively, the tube or tubes can themselves be passed under the drape or through the drape.

US2008/0004549 discloses a system for applying negative pressure on a wound which includes a device configured to provide negative pressure, a dressing sealably covering the wound and a spray-in foam located within the wound below the dressing material. Use of the spray-in foam overcomes the problem that a process of applying a dressing is tedious and time consuming. Unfortunately, US2008/0004549 does not suggest any material which would be suitable as a spray-in foam. Neither does the disclosure teach how the spray-in foam could, in practice, be applied at a wound site. In this sense the patent application is silent as to the necessary details which would enable a skilled person to use spray-in foam as suggested.

The technique suggested in US2008/0004549 is also prone to a problem caused as the foam is sprayed into a wound site. That is to say the foam rises up uncontrollably and would tend to spread too far vertically as well as over the peri-wound area. As such, the foam would require removing from around the wound to prevent skin maceration. Cutting or trimming wound fillers presents a risk to the clinician of leaving behind wound filler in a patient. This could hinder healing and may cause a rejection reaction from the patient's body a future date.

By adhering the drape securely to the peri-wound area (the healthy skin/dermis surrounding the wound), injected foam is prevented or substantially prevented from making contact with the healthy skin/dermal surface. It is well known to those in the art that wound exudate should be prevented, or at least try to prevent as much as possible from making contact with healthy skin/dermis.

For wounds that occur on awkward areas of the body, the packing of the wound can be problematical regardless of the prior known filling technique which is utilised. For example, if the wound is on the side or underside of a body then the filler can easily fall out before a clinician has an opportunity to apply the drape over the filler. Alternatively, the patient may be required to adopt an uncomfortable position in order to prevent the filler from falling out of the wound site. Even the spray in foam technique suggested in US2008/0004549 is prone to such a problem.

SUMMARY OF THE INVENTION

It is an aim of the present invention to at least partly mitigate the above-mentioned problems.

It is an aim of certain embodiments of the present invention to provide a method of dressing a wound prior to the application of negative pressure wound therapy in a prompt and efficient manner.

It is an aim of certain embodiments of the present invention to provide a method and apparatus for dressing a wound and a method of applying negative pressure at a wound site in which filler material is not prone to falling out of a wound or being partially dislodged from the wound.

It is an aim of certain embodiments of the present invention to provide a method of dressing a wound which can be applied to awkward areas of the body.

It is an aim of certain embodiments of the present invention to manufacture an improved wound dressing filler and/or wound dressing, having a filler.

The drape of the invention may be any known suitable medical drape in particular it may be a gas permeable or semi-permeable drape coated in a pressure sensitive adhesive, for example Opsite or Tegaderm or other well known drapes in the medical field. Suitably the drape will be a flexible drape. A flexible drape has the advantage of conforming to the treatment area. Also when injecting foam filler into an area enclosed, whether enclosed entirely substantially or partially, having a flexible drape helps ensure a smooth surface, but importantly minimises voids of no foam filler in the area under the drape. This is particularly important when the dressing is being used for negative pressure treatment.

This is also particularly important when the foam is only mixed immediately prior to injection as the foam may still be mixing and reacting to its final composition.

According to a first aspect of the present invention there is provided a method of providing a wound filler at a wound site prior to application of negative pressure wound therapy, the method comprising: securing at least one drape element over a wound site; and subsequently injecting filler material through at least one opening in the drape.

According to a second aspect of the present invention there is provided a method of providing negative pressure wound therapy at a wound site, comprising: securing at least one drape element over a wound site; subsequently injecting filler material through at least one opening in the drape element;

connecting the injected filler material to a source of negative pressure; and applying negative to the wound site pressure via said source.

According to a third aspect of the present invention there is provided a method of providing wound filler at a wound site, comprising: providing a wound cavity by covering a wound bed; and subsequently injecting filler material into the wound cavity.

According to some aspects of the present invention there is provided a process of manufacture of a wound dressing filler and/or wound dressing, the process comprising securing at least one drape element over a chosen site; and subsequently injecting wound dressing filler material through at least one opening in the drape.

Further this may be an in situ wound dressing and manufacture thereof. Certain embodiments of the present invention provide the advantage that a wound site is covered with a drape prior to the introduction of filler material. By covering a wound site with a drape a wound chamber region is generated which can then subsequently be filled with an injected material. This has the advantage that wound filler will conform intimately to a wound bed and also be prevented from falling out of a wound. The injected material can be any suitable material such as an injectable foam or string or the like. By the term "the cavity under the drape element" this also includes any cavity partially or substantially enclosed by the drape element not just strictly under.

Certain embodiments of the present invention provide an advantage that a wound chamber defined by a wound bed or wound contact layer and an overlying drape or other type of cover can be filled entirely with filler material. This has the advantage that the drape may fit and secure better at its chosen site as the entire cavity is filled with filler. This may obtain therefore a smooth surface; important for patient comfort should the patient lie on the dressing. This enhances the application of negative pressure across the whole wound bed as well as allowing fluid to be removed from all areas of the wound as there are no voids and/or less wringles in the drape.

BRIEF DESCRIPTION OF DRAWINGS

Embodiments of the present invention will now be described hereinafter, by way of example only, with reference to the accompanying drawings in which.

In the description like reference numerals refer to like parts.

DETAILED DESCRIPTION OF THE PREFERRED EMBODIMENTS

Figure 1:
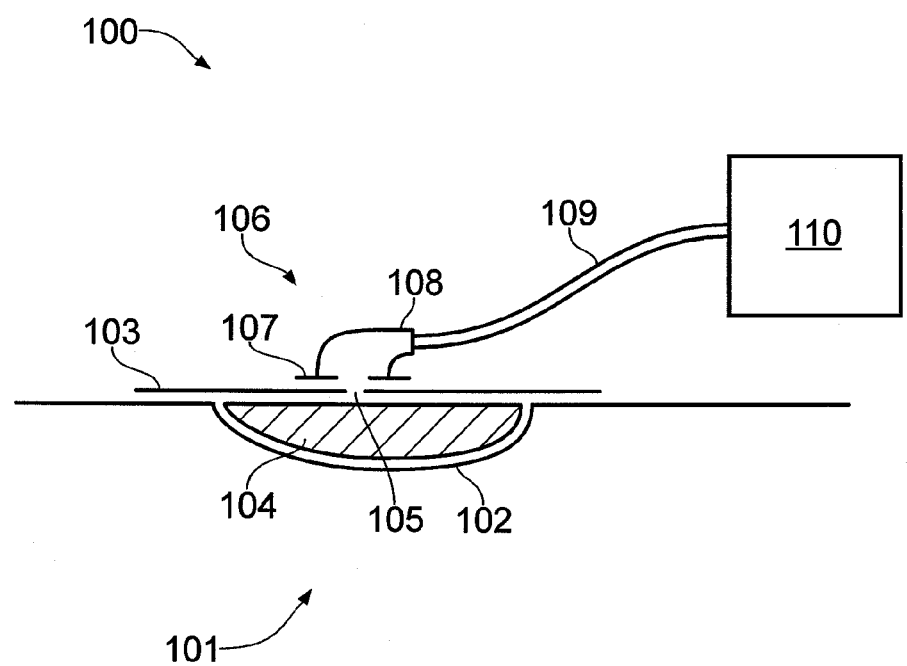
FIG. 1 illustrates the application of negative pressure wound therapy.

FIG. 1 illustrates a system (100) for applying negative pressure wound therapy (NPWT) at a wound site (101). The wound site is a region including a wound bed and surrounding skin. As illustrated in FIG. 1, the wound bed (102) is separated in a spaced apart manner from an overlying drape (103) by filler material (104). The drape (103) has an adhesive on a lower surface which enables the drape to be secured around the wound. Other ways of securing a cover over a wound bed are of course possible. An aperture (105) is formed in the drape and a suction head (106) is secured over the aperture.

The suction head (106) includes a flange (107) which encircles the aperture (105) and a spout (108) which is secured to a suction tube (109) leading to a vacuum pump system (110).

Alternative forms of negative pressure sources may be utilised according to certain embodiments of the present invention. For example, but not limited to, fixed displacement pumps, syringes, wall suction apparatus, mechanical pumps or the like.

Negative pressure generally refers to pressure less than ambient pressure at a wound site where treatment is to be carried out. Aptly the negative pressure is in the range −10 mmHg to −400 mmHg. Aptly the negative pressure applied is in the range −80 mmHg to −180 mmHg. Aptly the negative pressure applied is I the range −110 mmHg to −140 mmHg.

It will be appreciated that instead of a single suction tube (109) the pumping system (110) may be connected to the suction head (106) via a multi-lumen tube. Also the connecting tube (109) may be itself be formed as multiple tubes which might, from time to time, be connected and reconnected by some sort of coupling device to assist clinical staff.

Although not shown, the pumping system (110) will include a pump enabled to establish suitable ranges of negative pressure either continuously or intermittently and a collecting container such as a canister or bag or the like. One or more filters may be included to prevent contamination of the pumping unit when a disposable container is utilised or to help prevent odours escaping.

Figure 2:
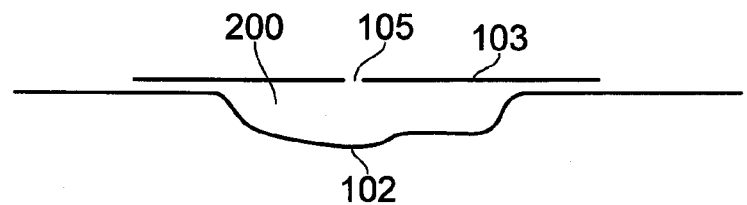
FIG. 2 illustrates covering a wound site with a drape.

FIG. 2 illustrates a wound cavity (200) formed between an upper surface of the wound bed (102) or overlying wound contact layer (not shown) and a lower surface of the drape (103). The wound site corresponds to a region of bodily tissue of any human, animal or other organism. This includes, but is not limited to, bone tissue, dermal tissue, connective tissue or the like. The wound site may include a wound, or defective tissue and/or healthy tissue.

FIG. 2 illustrates an early stage in the application of negative pressure wound therapy at a wound site. A wound and surrounding peri-wound area are prepared and then a drape is secured over the wound bed. Because there is no filler material which can fall out of a wound, healthcare providers have an excellent opportunity to provide a good seal by carefully securing the drape around the wound to ensure a good seal is generated. A hole is then made in the drape by the healthcare provider. Alternatively, a hole may be made in the drape at any point before application to the wound.

An in-situ forming wound filler is applied to the wound site after the drape has been attached to the patient. It has been found that, for example, a liquid foam forming material can be injected through an aperture in the drape to form the filler in the wound chamber. Suitable injectors could be any suitable injector known in the art, these include but not limited to, syringes, double barrel syringes, aerosols, injection guns, dynamic mixers, power mixers and or static mixers 2 or more part static mixers. Suitably a 2 part static mixer could be used for the present invention.

As such, the filler will conform intimately to the wound bed and also be prevented from falling out of the wound by the pre-arranged drape. This enables wounds to be dressed for NPWT on all parts of a body single-handedly or without the need for many assistants without placing a patient in an awkward position. It is advantageous when applying the filler to wounds, for example, on a side of a body, that an aperture in the drape is placed towards the top of the drape in order to allow the injected filler material to fill the cavity from the bottom up.

It will be appreciated that optionally a wound liner can be placed in the wound prior to application of the drape and subsequent in situ forming filler. This may have the advantage of preventing skin formation at the base of the filler material in use.

There are many different materials which are capable of forming a porous structure from liquid starting components. For example, suitable materials are those based on two-part polyurethane chemistry and are formed by mixing an isocyanate pre-polymer with a water/surfactant phase. The isocyanate reacts with the water to cross-link the pre-polymer and at the same time liberate carbon dioxide to produce a porous structure.

Advantageously, formulations are used which cure in less than five minutes. Silicon-based foams are also suitable for use with the present invention. Such materials are two-component liquid systems capable for forming a porous structure. An example is Cavi-care™. Cavi-care™ is a two-part room-temperature vulcanising foam, produced from a polydimethylsiloxane base, a platinum catalyst and hydrogen gas-releasing agent which react together to form a soft-pliable, slightly absorbent white foam. Such material typically cures in around two minutes.

Use of hydrogen as a blowing agent i.e. using a hydrogen gas releasing agent, is advantageous as the small molecule size of hydrogen allows for rapid diffusion through a gas permeable or semi-permeable drape.

Suitably the present invention would be with a solventless system for forming the porous structure for the area under the drape. This could be for instance a 2 part solventless system to produce a porous foam filler in the area under the drape. Rapid gas release through the drape allows for a uniform density, highly porous foam to be generated under the drape. In this way foams of uniform pore size are produced in the enclosure under the drape.

An advantage of the present invention is that the porous structure under the drape is produced in situ. The liquid components are reacting or foaming under the drape to produce the finished dressing and/or dressing filler.

This has many advantages including ensuring an intimate contact with the wound surface.

One advantage that is special to the present invention is the use of a solventless system to produce the porous filler to be situated under the drape.

Certain embodiments of the present invention are directed to the use of solventless systems to produce the porous filler. Such foaming systems only produce gas as a by product when reacting/foaming to produce the final solid/semi-solid product as a filler e.g. foam.

The advantage of having only a gas e.g. Hydrogen as a by product to the reaction, under the drape, to produce the filler of the dressing is that this quickly escapes the dressing through the drape or the edges of the drape to skin contact or indeed the orifice in which the filler was injected. Further it will be appreciated that solvents require heat to change phase from liquid to gas and this heat must be taken from the foam and its surrounding atmosphere, which may include the wound itself. Cooling of a wound may delay healing and cause discomfort to the patient therefore it is to be avoided. Therefore, a further advantage of solventless systems is that there is no endothermic effect on the wound.

Use of solvent based systems to produce the final solid/semi-solid filler under the drape may have the disadvantage of getting rid of the solvent from under the drape and indeed the solvent may be harmful to a patient.

As mentioned above a solventless system in which the filler is produced under the drape in situ, i.e. where the filler is still reacting under the drape to produce its final form has the advantage among other things to enable a good intimate contact with the wound surface.

This intimate contact with the wound surface free of large voids etc is important when the dressing is intended to be used with negative pressure wound therapy.

Aptly the present invention uses a 2 component liquid solventless system to react under the drape to produce a solid porous filler, for example a porous foam filler.

Still this may be silicon based or a polyurethane based for example, porous fillers or porous foam fillers.

Producing only gas as a reacting by product under the drape when producing the final solid/semi solid filler allows a wider range of drapes to be used.

Figure 3:
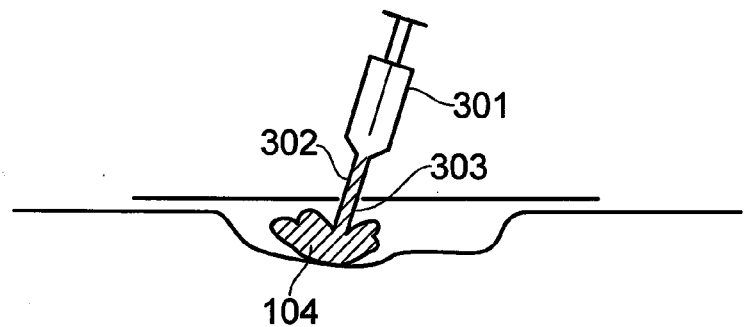
FIG. 3 illustrates injecting filler through an aperture in a drape.

The in-situ forming components of Cavi-care™ can be packaged in a double-barrel syringe (301) of the type illustrated in FIG. 3 which is equipped with a static mixer (302).

Figure 4:
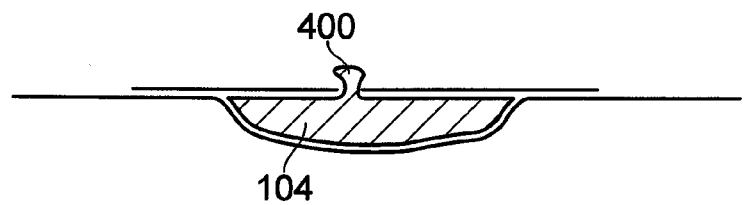
FIG. 4 illustrates removal of excess filler.

Dispensing the reactive components, to the wound, through the static mixer (302) causes a chemical reaction to start which then continues in the wound chamber under the drape (103). It has been found that expansion within the wound chamber against the closed wound bed and closed drape surprisingly allows the injected material to generate a foam without causing the overlying drape to lift away from the wound bed. As illustrated in FIG. 4 instead of the drape lifting away from the wound bed injected filler material which is surplus to requirements to fill the wound chamber (200) merely escapes through the aperture during the injection process. The excess material (400) can then simply be removed by clinical staff using scissors or a knife. During the injection phase, as illustrated in FIG. 3, the nozzle (303) of the syringe (301) can be used to urge the injected filler throughout the wound cavity. This is particularly advantageous to ensure that the filler abuts the wound edge regions and thus completely fills the wound cavity. Subsequent to injecting the filler the excess material is removed and once completely cured, the suction head (106) can be secured over the aperture (105) and negative pressure wound therapy can begin.

Figure 5:
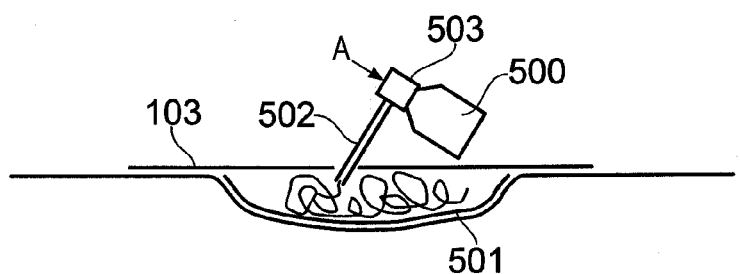
FIG. 5 illustrates injecting string like filler material.

FIG. 5 illustrates an alternative embodiment of the present invention in which instead of the double-barrel syringe (301) used to inject a filler material a pressurized canister (500) is utilised to inject string-like filler material into a wound cavity. FIG. 5 also illustrates an optional wound contact layer (501) which, as noted above, might also be used with the previously referred-to embodiment.

In order to utilise the string-like filler material a wound bed is first covered by a wound contact layer (501) and then a drape (103) is secured over the wound site. The drape is secured to provide a leak-free seal around the wound bed. An aperture (103) is preformed in the drape (103) or is then generated in the drape by clinical staff. The pressurised canister (500) contains pre-stored material under pressure and this is released along a dispensing nozzle (502) when a user presses a cap (503) in the direction A shown in FIG. 5. The filler material stored in the canister (500) is then released along the nozzle (502) and injected into the wound chamber as a string. As this string cures a porous lattice structure is generated in the wound chamber. As with the previous embodiment the nozzle can be used to ensure the filler reaches all regions within the wound cavity.

Embodiments of the present invention provide the advantage that a filler can be formed suitable for the application of NPWT which conforms intimately with a wound bed or wound contact layer and is also prevented from falling out of a wound by a pre-arranged drape. This means that it is possible to dress wounds with a filler for NPWT on all parts of the body, either via a single person or with minimal assistance.

This also avoids the need to place a patient in awkward position or helps keep such placement to a minimum.

An example of one embodiment of the present invention but not limited to maybe, the process comprising:
securing at least one drape element over a chosen site; and
subsequently injecting a liquid state wound dressing filler material through at least one opening in the drape, in which under the drape the liquid state wound dressing filler is reacting giving off gas and subsequently hardens to a solid/semi-solid porous wound filler under the drape.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. A method of providing wound filler at a wound site prior to application of negative pressure wound therapy, the method comprising:
   first, securing a drape over a wound cavity to form a seal;
   second and subsequently to forming the seal, injecting a liquid foam filler material through an aperture in the drape, the liquid foam filler material configured to expand outward as the liquid foam filler material cures into a solid and substantially fills an entire volume of the wound cavity, the liquid foam filler material applying an outward force a against the wound cavity and the drape and thereby directing the expanding foam filler through the aperture without causing the seal to lift away from the wound cavity; and
   third, removing excess foam filler material which flows out through the aperture.

2. The method as claimed in claim 1, wherein the foam filler cures into the form of an elongated string, the elongated string comprising a porous lattice structure.

3. The method as claimed in claim 1, further comprising:
   forming a porous structure by injecting a pre-mixed biocompatible foam.

4. The method as claimed in claim 1, further comprising:
   lining a wound bed at the wound site with a liner element prior to securing the drape over the wound site.

5. The method as claimed in claim 1, further comprising:
   locating a fluid communication port over each opening in the drape.

6. The method as claimed in claim 1, further comprising:
   urging injected filler material into peripheral regions of a wound cavity under the drape prior to allowing the filler material to set or curing the filler material.

7. The method as claimed in claim 6, further comprising:
   injecting the filler material with an injector apparatus comprising a nozzle member; and
   urging the filler material with the nozzle member.

8. The method as claimed in claim 1, wherein removing excess filler material comprises cutting off semi-solid filler material subsequent to drape the material having flowed out through the aperture.

9. The method as claimed in claim 1, wherein connecting the injected filler material comprises:
   securing a suction port comprising a spout member and a flange member over each opening in the drape; and
   securing a distal end of a suction lumen to the spout member of the suction port.

10. The method of claim 1, wherein removing excess filler material comprises removing an outer skin layer of the filler material.

11. The method of claim 10, wherein the outer skin layer comprises a section of foam that has cured into a structure that will not transmit negative pressure.

12. A method of providing negative pressure wound therapy at a wound site, comprising:
    first, securing at least one drape over a wound site to form a seal;
    second and subsequently to forming the seal, injecting filler material through at least one opening in the drape, the filler material configured to expand and fill a wound cavity under the drape, the filler material further configured to apply an outward force to the wound and the drape without causing the seal to lift away from the wound cavity;
    third, fluidically connecting the injected filler material to a source of negative pressure; and
    fourth, applying negative to the wound cavity pressure via said source.

13. The method as claimed in claim 12, further comprising:
    urging injected filler material into peripheral regions of a wound cavity under the drape prior to allowing the filler material to set or curing the filler material.

14. The method as claimed in claim 13, further comprising:
    injecting the filler material with an injector apparatus comprising a nozzle member; and
    urging the filler material with the nozzle member.

15. The method as claimed in claim 12, wherein applying negative pressure comprises one of selectively, continuously, or intermittently applying a predetermined negative pressure via a suction pump.

16. The method as claimed in claim 12, further comprising removing excess filler material that flows through an opening in the drape.

17. The method as claimed in claim 12, wherein the filler material is in the shape of an elongated string.

18. The method as claimed in claim 7, wherein the injector apparatus comprises two chambers and a static mixer.

* * * * *

UNITED STATES PATENT AND TRADEMARK OFFICE
CERTIFICATE OF CORRECTION

PATENT NO. : 8,998,866 B2  
APPLICATION NO. : 13/806722  
DATED : April 7, 2015  
INVENTOR(S) : Hicks Page 1 of 1

It is certified that error appears in the above-identified patent and that said Letters Patent is hereby corrected as shown below:

On the title page item [56],

Column 2 page 4 line 23, Under Other Publications, change "EIMJM" to --IMJM--.

In the specification

Column 4 line 55, Change "and or" to --and/or--.

Column 5 line 47, Change "by product" to --byproduct--.

Column 5 lines 50-51, Change "by product" to --byproduct--.

Column 6 lines 18-38, Delete "Dispensing the reactive components, to the wound... pressure wound therapy can begin." and insert the same on Col. 6, Line 17, as the continuation of the same Paragraph.

In the claims

Column 7 line 56, Claim 1, change "a against" to --against--.

Signed and Sealed this  
Fifteenth Day of December, 2015

Michelle K. Lee  
*Director of the United States Patent and Trademark Office*